United States Patent
Chen et al.

(10) Patent No.: US 10,445,932 B2
(45) Date of Patent: Oct. 15, 2019

(54) RUNNING EXERCISE EQUIPMENT WITH ASSOCIATED VIRTUAL REALITY INTERACTION METHOD AND NON-VOLATILE STORAGE MEDIA

(71) Applicant: Shanghai zhangmen science and Technology Co., Ltd., Shanghai (CN)

(72) Inventors: Danian Chen, Shanghai (CN); Zhengxiang Gu, Shanghai (CN)

(73) Assignee: SHANGHAI ZHANGXIAN NETWORK TECHNOLOGY CO., LTD., Shanghai (CN)

(*) Notice: Subject to any disclaimer, the term of this patent is extended or adjusted under 35 U.S.C. 154(b) by 84 days.

(21) Appl. No.: 15/678,112

(22) Filed: Aug. 16, 2017

(65) Prior Publication Data

US 2018/0053349 A1 Feb. 22, 2018

(30) Foreign Application Priority Data

Aug. 16, 2016 (CN) .......................... 2016 1 0673438

(51) Int. Cl.

| G06T 19/00 | (2011.01) |
|---|---|
| G06F 3/01 | (2006.01) |
| G06K 9/00 | (2006.01) |
| G06F 1/16 | (2006.01) |
| G16H 20/30 | (2018.01) |
| A63B 24/00 | (2006.01) |
| A63B 22/02 | (2006.01) |

(Continued)

(52) U.S. Cl.
CPC ............ G06T 19/003 (2013.01); G06F 1/163 (2013.01); G06F 3/011 (2013.01); G06F 3/016 (2013.01); G06K 9/00342 (2013.01); G06T 19/006 (2013.01); G16H 20/30 (2018.01); *A63B 22/02* (2013.01); *A63B 69/0064* (2013.01); *A63B 2022/0271* (2013.01); *A63B 2022/0278* (2013.01); *A63B 2024/009* (2013.01); *A63B 2071/0638* (2013.01); *A63G 31/16* (2013.01)

(58) Field of Classification Search
CPC ...... A63B 2024/009; A63B 2071/0638; A63B 2071/0644; A63B 2220/18; A63B 24/0062; A63B 71/0622; A63B 22/0023; A63B 2220/20; A63B 2220/30; A63F 13/212; G06F 1/163; G06F 3/011; G06F 3/016; G06T 19/006; G06K 9/00342
See application file for complete search history.

(56) References Cited

U.S. PATENT DOCUMENTS

| 2011/0164044 A1* | 7/2011 | Huang ............... A63B 21/0004 345/473 |
| 2012/0040798 A1* | 2/2012 | Yu ...................... A63B 22/0242 482/4 |

(Continued)

*Primary Examiner* — Jin Cheng Wang
(74) *Attorney, Agent, or Firm* — Gokalp Bayramoglu

(57) ABSTRACT

The present invention provides a running exercise equipment and a virtual reality interaction method thereof, in combination with virtual reality technology. The method includes: generating a virtual scene to the user based on the scene data; acquiring behavior data of a user when the user performs an action according to the virtual scene; generating scene update information based on the behavior data of the user, updating the scene data according to the scene update information; and controlling an action of the running exercise equipment according to the scene update information.

18 Claims, 5 Drawing Sheets

(51) Int. Cl.
    *A63G 31/16*     (2006.01)
    *A63B 69/00*     (2006.01)
    *A63B 71/06*     (2006.01)

(56) References Cited

U.S. PATENT DOCUMENTS

| | | | |
|---|---|---|---|
| 2013/0267385 A1* | 10/2013 | Watterson | A63B 24/0062 |
| | | | 482/8 |
| 2014/0024500 A1* | 1/2014 | Watterson | A63B 22/02 |
| | | | 482/54 |
| 2014/0082526 A1* | 3/2014 | Park | H04L 65/403 |
| | | | 715/757 |
| 2016/0250519 A1* | 9/2016 | Watterson | A63B 24/0075 |
| | | | 482/4 |
| 2016/0317866 A1* | 11/2016 | Fung | A63B 24/0003 |
| 2016/0339300 A1* | 11/2016 | Todasco | H04W 4/80 |
| 2017/0046600 A1* | 2/2017 | Lim | G06K 9/00342 |
| 2018/0224930 A1* | 8/2018 | Folmer | A63F 13/211 |

\* cited by examiner

RUNNING EXERCISE EQUIPMENT WITH ASSOCIATED VIRTUAL REALITY INTERACTION METHOD AND NON-VOLATILE STORAGE MEDIA

CROSS REFERENCE TO RELATED APPLICATIONS

This application is based upon and claims priority to Chinese Patent Application No. CN 201610673438.5 (CN), filed on Aug. 16, 2016, the entire content of which is incorporated herein by reference.

TECHNICAL FIELD

The application relates to the field of virtual reality technology, particularly relating to a running exercise equipment with an associated virtual reality interaction method and a non-volatile storage media based on the running exercise equipment.

BACKGROUND

The treadmill is a conventional fitness device used at home and gym. The principle of the treadmill is to control the driving speed of the running belt to simulate that the user is running forward, and the user running on the treadmill will remain in place. As the treadmill is generally placed indoors in a fixed position, so the user can see indoor scene when running.

SUMMARY OF THE INVENTION

Based on one aspect of the present invention, a virtual reality interaction method of the running exercise equipment is provided. The method includes: providing a virtual scene to the user according to the scene data; acquiring behavior data of a user when the user performs an action according to the virtual scene; generating scene update information based on the behavior data of the user, and updating the scene data according to the scene update information; controlling the action of the running exercise equipment according to the scene update information.

Based on one aspect of the present invention, a non-volatile storage medium is provided, and one or more instructions are stored in the non-volatile storage medium. Wherein the one or more instructions are executed by the processor to cause the processor to: providing a virtual scene to the user based on the scene data; acquiring behavior data of a user when the user performs an action according to the virtual scene; generating scene update information based on the behavior data of the user and updating the scene data based on the scene update information; and controlling the action of the running exercise equipment according to the scene update information.

Based on another aspect of the present invention, a running exercise equipment is provided, including: one or more processors, a non-volatile storage medium storing one or more computer-readable instructions. When one or more of the computer-readable instructions are executed by the one or more processors to cause the one or more processors to: providing a virtual scene to the user based on the scene data; a acquiring behavior data of a user when the user performs an action according to the virtual scene; generating scene update information based on the behavior data of the user and updating the scene data based on the scene update information; and controlling the action of the running exercise equipment according to the scene update information.

BRIEF DESCRIPTION OF THE DRAWINGS

By reading the following detailed description of non-limiting embodiments with reference to the accompanying drawings, the other features, objects, and advantages of the present invention will become more apparent:

FIG. 1 (b) is a layout schematic diagram of all the parts in the running exercise equipment provided by the embodiment of the present invention;

FIG. 3 (b) is a structural schematic diagram of a running device of another running exercise equipment provided by the embodiment of the present invention;

The same or similar parts are represented by the identical or similar reference numbers in the drawings.

DETAILED DESCRIPTION OF THE INVENTION

The present invention will now be described in further detail with reference to the accompanying drawings.

Figure 1:
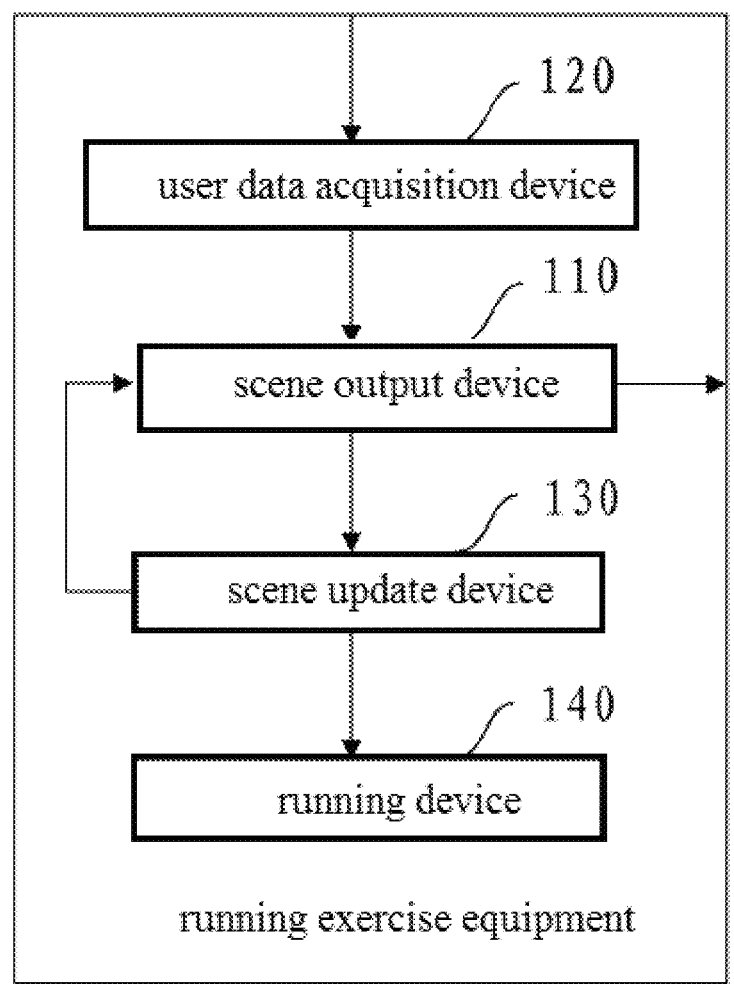
FIG. 1 (a) is a structural schematic diagram of a running exercise equipment provided by an embodiment of the present invention.
Figure 1:
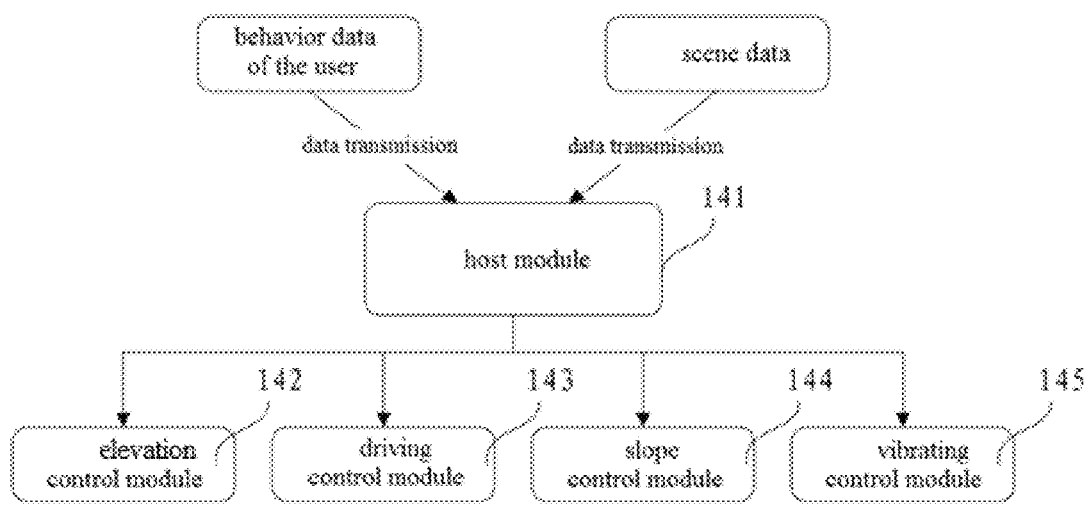

FIG. 1 (a) shows a schematic structural diagram of a running exercise equipment provided by an embodiment of the present invention. The running exercise equipment includes scene output device 110, user data acquisition device 120, scene update module 130, and running device 140. Wherein scene output device 110 is configured to provide a virtual scene to the user based on the scene data. User data acquisition device 120 is configured to acquire behavior data of a user when the user performs an action according to the virtual scene. Scene update module 130 is configured to generate scene update information based on the behavior data of the user and update the scene data based on the scene update information. Running device 140 is configured to control the action of the running exercise equipment according to the scene update information.

The solution combines the running exercise equipment with the virtual reality technology to provide the virtual scene to the user according to the preset scene data, so that the scene that the user sees is no longer confined to the place where the running exercise equipment is placed, and the user will perform the corresponding actions based on the virtual scene. The scene update information is generated by acquiring the behavior data of the user when performing actions, thereby updating the scene data, so that the virtual scene provided to the user can be advanced and changed according to the actions of the user. At the same time, the actions of the running exercise equipment are controlled based on the scene update information, so that the user is capable of physically obtaining the physical experience caused by change of the scene, thereby improving the user experience when exercising on the running exercise equipment.

In the practical application scenes, scene output device 110 according to some embodiments may specifically use a VR (Virtual Reality) helmet, VR glasses, a projection screen, and other devices. The user is capable of seeing the provided virtual scene through the scene output device. The scene data may be pre-stored in the memory of the running exercise equipment, and invoked and parsed by the scene output device when necessary, thereby providing the user with a corresponding virtual scene. The virtual scene is an environmental picture composed of images of ground, roads, buildings, plants, etc. As for the user of the running exercise equipment, the virtual scene may preferably be an outdoor environment picture suitable for a user's running exercise, such as woods, sports field etc., to give the user a real outdoor sport experience.

User data acquisition device 120 according to some embodiments may specifically use a 3D (Three Dimensions) camera, a three-axis gyroscope, and various types of sensors for capturing user's action characteristic information and sign information. Take the 3D camera as an example, a plurality of 3D cameras may be provided and distributed around the user, to capture the user's motion postures in real time and convert the motion postures into the human spatial motion vector matrix in real time. The coordinates of the vector matrix may include a human key feature point matrix, motion trend and velocities related to the feature point matrix, the displacement coordinates related to the feature point matrix. The above vector matrix may represent the action changes of the user when the actions are performed. The three-axis gyroscope and various types of sensors may be worn directly by the user, to detect the location changes and physical reactions when the actions are performed by the user, and obtain the corresponding data, including action characteristic information of the action changes and the sign information representing the user's physical reactions.

As a preferred embodiment, when the sign information such as heart rate, blood pressure, etc., are collected by user data acquisition device 120, the sign information may be provided to the user in real time, so that the user is capable of actively adjusting the exercise intensity based on the current sign information. Thus, scene output device 110 is also used to provide the sign information to the user. Specifically, the sign information may be provided to the user via image display or voice broadcast, etc., in addition to displaying the virtual scene by scene output device 110.

Scene update module 130 according to some embodiments is a processor for performing corresponding processing based on the behavior data. The processor may be integrated in the VR helmet, VR glasses as scene output device 110, or may be integrated in the host module. The scene update module is used to generate scene update information based on the action characteristic information and the sign information of the user, and update the scene data based on the scene update information.

The scene update information according to some embodiments is referred to as the corresponding changes of the virtual scene, which is generated based on the collected user's behavior data. For example, when the user is running straight forward, the buildings, trees, etc. in the virtual scene need to go backward. When the user runs faster, the buildings, trees and other objects also go backward faster, so as to meet the real situation. After the scene update information of the backward scene is generated based on the behavior data of the user, who moves forward, the scene data is updated based on the scene update information, so that a virtual scene conforming to the real situation may be continuously provided to the user by scene output device 110, based on the updated scene data, so as to continuously facilitate a steady run, an accelerated run, a turn and other actions performed by the user according to the changes in the virtual scene.

Figure 3:
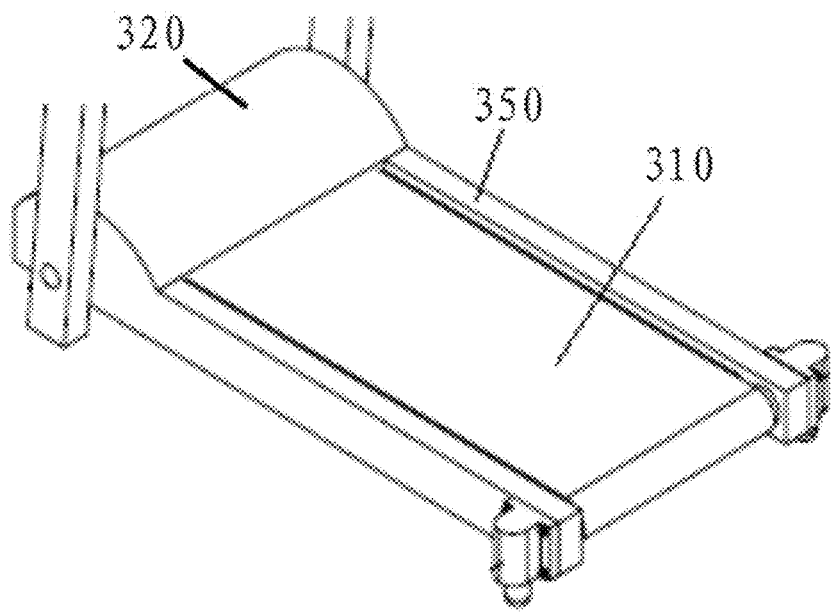
FIG. 3 (a) is a structural schematic diagram of a running device of the running exercise equipment provided by the embodiment of the present invention.
Figure 3:
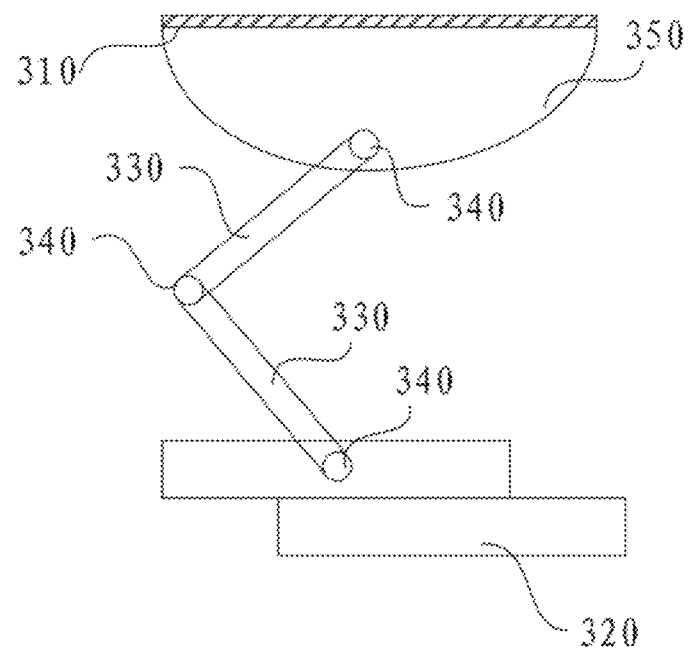

In order to realize the fundamental functions of the running exercise equipment, running device 140 according to some embodiments may specifically include running platform 350, running belt 310 arranged on running platform 350, and motor 320 for driving running belt 310, and the specific structures are shown in FIG. 3 (a). The motor may be a servo motor. When using the running exercise equipment, the user is capable of standing on the running belt of the running platform, and then the running belt is driven by the servo motor to achieve a basic straight running function.

Another embodiment of the present invention further provides a more preferred implementation, to better simulate a complex running scene. Running device 140 includes host module 141, a drive control module of the corresponding action. The drive control module of the corresponding action may include any one or a combination of elevation control module 142, driving control module 143, slope control module 144, and vibration control module 145. FIG. 1 (b) shows a structural schematic diagram of an embodiment. In order to ensure that the user can feel the real scene, the running device needs to control the action of the running exercise equipment according to the scene update information. For example, when the user's running path needs to be turned, uphill or downhill in the virtual scene, the running device needs to adjust the running belt correspondingly. For example, the slope of the runway is changed, the runway is raised, the moving speed of the runway is decreased, etc., to simulate the real body sense of the user in the current virtual scene.

For example, when the up and down movement of the running belt needs to be adjusted, the host module is configured to acquire the first action control information based on the scene update information, wherein the first action control information includes a up and down moving distance and up and down moving time of the running belt. The elevation control module is configured to adjust the up and down moving action of the running belt according to the first action control information, so as to make the user perceive a different gravitational acceleration. It is necessary to use the elevation control module to perform the up and down movement control of the running belt when the user performs actions such as an uphill movement, a downhill movement, a jump.

When the driving speed of the running belt needs to be adjusted, the host module is configured to acquire the second action control information based on the scene update information, wherein the second action control information includes a driving speed of the running belt. The driving control module is configured to adjust the driving action of the running belt according to the second action control information. It is necessary to use the driving control module to perform the driving speed control of the running belt when the user performs an action such as an accelerated or decelerated run.

When the slope of the running belt needs to be adjusted, the host module is configured to acquire the third action control information based on the scene update information, wherein the third action control information includes a tilt angle and tilt time of the running belt. The slope control module is configured for adjusting a tilt action of the running belt according to the third action control information. By controlling different tilt angles of the running belt, various scenes, such as the up and down slope, the left and right slope, or combinations thereof may be simulated. It is necessary to use the slope control module to control the slope of the running belt when the user is located on a sloping road or running uphill or downhill.

When the vibration of the running belt needs to be controlled, the host module is configured to acquire the fourth action control information based on the scene update information, wherein the fourth action control information includes vibration intensity and vibration time of the running belt. The vibration control module is configured for adjusting the vibration action of the running belt according to the fourth action control information, to simulate the vibration of the ground in the virtual scene or send an alarm or prompt to the user through the vibration.

In the practical application, the specific structure according to some embodiments of running device 140 is shown in FIG. 3 (*b*). The running device may be implemented in the form of a central control device in conjunction with an action platform, wherein the central control device is used for processing the control information, example, generation of the first, second, third and fourth action control information described above may be realized by any form of chip, circuit, processor, etc., (not shown in the drawings). The action platform is used to generate the corresponding action according to the control information, so as to achieve the purpose of simulating the real running scene. Specifically, the action platform includes running platform 350, running belt 310, motor 320, driving shaft 330, and universal bearing 340. Running belt 310 is provided on running platform 350 for carrying a user. The specific form of the running belt may include, but is not limited to a linear runway of a conventional treadmill and other irregularly shaped runways, such as a circular runway. Motor 320 is connected to running belt 310 for driving the running belt, so as to adjust the driving speed of the running belt. In addition, the motor 320 may realize the control of the height, the slope, the vibration of running platform 350 by controlling the action changes of drive shaft 330 and universal bearing 340, so that the complex action control and the realistic simulation of the real running scene may be achieved. Preferably, the motor may also be a servo motor.

Figure 2:
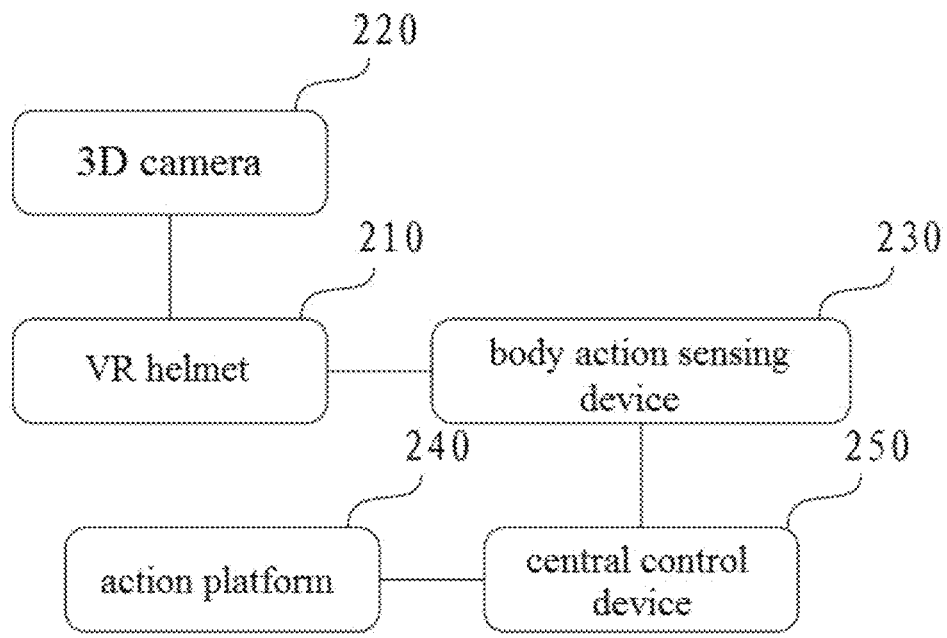
FIG. 2 is a structural schematic diagram of another running exercise equipment provided by the embodiment of the present invention.

FIG. 2 shows a schematic structural diagram of a running exercise equipment provided by another embodiment of the present invention. The running exercise equipment includes VR helmet 210, 3D cameras 220, body action sensing device 230, action platform 240, and central control device 250. 3D cameras 220 are connected to VR helmet 210 and distributed around the action platform. Central control device 250 is connected to action platform 240 and body action sensing device 230 respectively. VR helmet 210 is connected to body action sensing device 230. In the embodiment, the connection among the various components may be wireless or wired depending on the actual demand.

Wherein VR helmet 210 according to some embodiments is worn by a user for providing a virtual scene to the user based on the scene data, so that the user performs an action according to the virtual scene. VR helmet 210 includes at least a memory, a processor, and a picture output module. The scene data is stored in the memory of the VR helmet, and when the scene data needs to be displayed to the user, the scene data is read by the processor and the picture output module is invoked to supply the picture corresponding to the scene data to the user. Further, the VR helmet may also include an audio player, a microphone and other audio-related devices, so as to input and output the audio in cooperation with the image.

3D cameras 220 according to some embodiments are used for collecting the images of the user's body, and sending the collected image to the VR helmet. The image data are processed by the processor to obtain the action characteristic information of the user. As an alternative, the image may be processed by the processor owned by the 3D cameras, and then the action characteristic information of the user is sent to VR helmet 210. In addition to that the 3D cameras are used to obtain the action characteristic information of the user, besides, the 3D cameras are also used to acquire the images of the user's body and project the images into the virtual scene after processing. For example, multiple running exercise equipment may interact through the network. The user's body images collected by the 3D cameras of each running exercise equipment may be sent to the VR helmet of the other running exercise equipment, which may project the body images of the users of another running exercise equipment on the basis of the virtual scene of the present device, so that the user of each running exercise equipment is capable of seeing other users in his/her own virtual scene. Thus, the users is capable of further interacting with each other, to improve the user's interactive experience.

Body action sensing device 230 according to some embodiments may include a head rotation and direction sensor, a foot pressure measurement sensor, a leg and arm motion amplitude sensor, etc., for collecting the rotational movement and direction of the user's head, the pressure distribution of the foot, the leg and arm movement amplitude and the muscle electrical signal of the user. The electrical signal includes the action characteristic information and the sign information of the user, and the electrical signal is transmitted to VR helmet 210 and central control device 250, for calculating the scene update information used for updating the scene data and various action control information for driving the action platform to perform the corresponding actions. Hereon, any two or all, the processor of VR helmet 210, the processor of 3D camera 220, and central control devices 250 may be integrated together. For example, all the processing operations are integrated and performed in the central control device. When using running exercise equipment, the user is running on action platform 240, and action platform 240 may adjust the height, slope, driving speed, and vibration according to the changes of the virtual scene.

Figure 4:
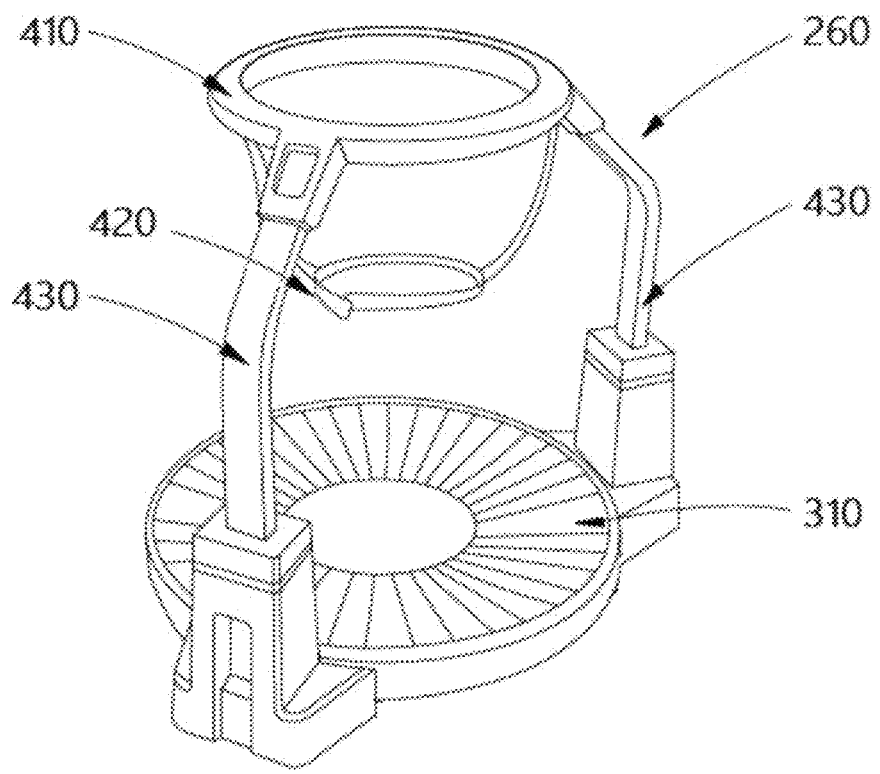
FIG. 4 is a structural schematic diagram of a protective device in a running exercise equipment provided by the embodiment of the present invention.

As a preferred embodiment, the running exercise equipment further includes protection device 260 for preventing the user from falling in the movement, and protection device 260 is provided on runway 310. For example, the protection device may use the structure as shown in FIG. 4, including lumbar protection disk 410, fastening strap 420, and fixing support bar 430. Fixing support bar 430 is provided on the runway and used for supporting lumbar protection disk 410. In order to ensure stability, at least two or more fixing support bars 430 are used. Fastening strap 420 is attached to lumbar protection disc 410 or fixing support bar 430. The user stands in lumbar protection disc 410 when using the running exercise equipment, and the body is bound by fastening strap 420, so as to effectively prevent the user from falling during the movement.

Figure 5:
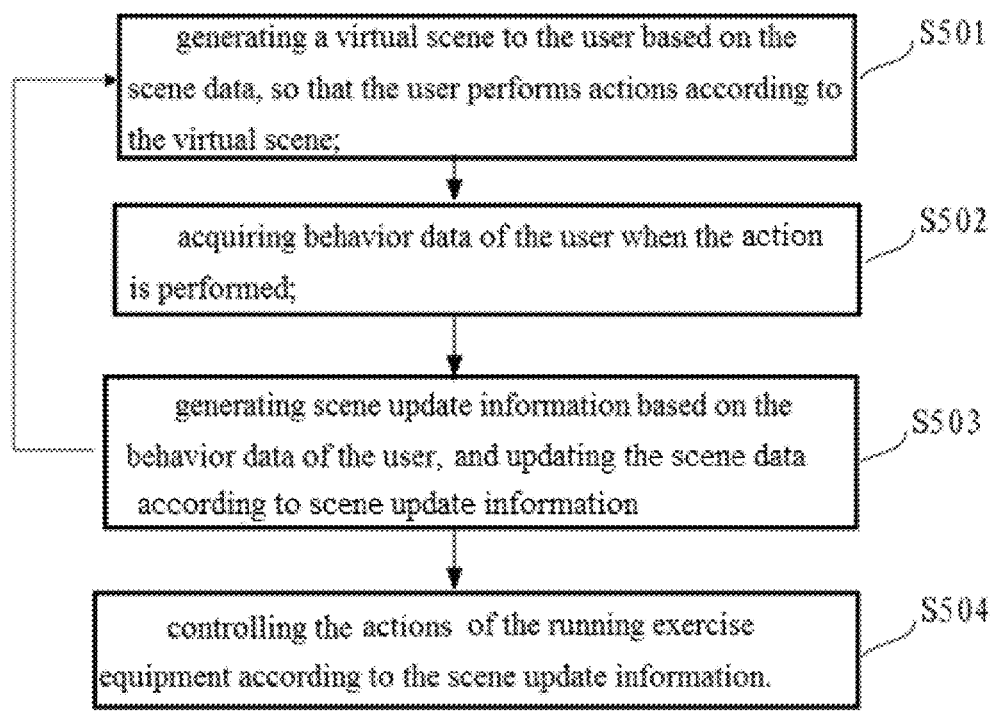
FIG. 5 is a flow chart of a virtual reality interaction method of the running exercise equipment provided by the embodiment of the present invention.

Based on another aspect of the present invention, a virtual reality interaction method of a running exercise equipment is provided, the flow chart of the method is shown in FIG. 5, including the steps as below:

Step S501, A virtual scene is provided to the user based on the scene data, so that the user performs an action according to the virtual scene.

Step S502, The behavior data of the user is collected when the action is perform ed.

Step S503, The scene update information is generated based on the behavior data of the user and the scene data is updated based on the scene update information.

Step S504, The action of the running exercise equipment is controlled based on the scene update information.

The solution combines the running exercise equipment with the virtual reality technology to provide the virtual scene to the user based on the preset scene data, so that the scene that the user sees is no longer confined to the place where the running exercise equipment is placed, and the user will perform the corresponding actions based on the virtual scene. The scene update information is generated by acquiring the behavior data of the user when performing actions, thereby updating the scene data, so that the virtual scene provided to the user may be advanced and changed according to the actions of the user. At the same time, the actions of the running exercise equipment are controlled based on the scene update information, so that the user is capable of physically obtain the physical experience caused by change of the scene, thereby improving the user experience when exercising on the running exercise equipment.

In the practical application scenes, the step S501 may be implemented by the scene output device of the running exercise equipment accordingly. The scene output device may specifically use a VR (Virtual Reality) helmet, VR glasses, a projection screen, and other devices: The user may see the provided virtual scene through the scene output device. The scene data may be pre-stored in the memory of the running exercise equipment, and invoked and parsed by the scene output device when necessary, thereby providing the user with a corresponding virtual scene. The virtual scene is an environmental picture composed of images of ground, roads, buildings, plants, etc. As for the user of the running exercise equipment, the virtual scene may preferably be an outdoor environment picture suitable for a user's running exercise equipment, such as woods, sports field etc., to give the user a real outdoor sport experience.

The step S502 may be implemented by the user data acquisition device of the running exercise equipment accordingly. The user data acquisition device may specifically use a 3D (Three Dimensions) camera, a three-axis gyroscope, and various types of sensors for capturing user's action characteristic information and sign information. Take the 3D camera as an example, a plurality of 3D cameras may be provided and distributed around the user, to capture the user's sport postures in real time and convert the sport postures into the human spatial movement vector matrix in real time. The coordinates of the vector matrix may include a human key feature point matrix, motion trend and velocities related to the feature point matrix, the displacement coordinates related to the feature point matrix. The above vector matrix can represent the action changes of the user when the actions are performed. The three-axis gyroscope and various types of sensors may be worn directly on the user, to detect the location changes and physical reactions when the actions are performed by the user, and obtain the corresponding data, including action characteristic information of the action changes and the sign information representing the user's physical reaction.

As a preferred embodiment, when the sign information, such as heart rate, blood pressure, etc., are collected by the user data acquisition device, the sign information may be provided to the user in real time, so that the user is capable of actively adjusting the exercise intensity based on the current sign information. Thus, the scene output device is also used to provide the sign information to the user. Specifically, the sign information may be provided to the user via image display or voice broadcast, etc., when displaying the virtual scene by the scene output device.

The step S503 may be implemented by the scene update module of the running exercise equipment accordingly. The scene update module is a processor for performing a corresponding processing based on the behavior data. The processor may be integrated in the VR helmet, VR glasses as the scene output device, also may be integrated in the host module. The scene update module is used to generate scene update information based on the action characteristic information and the sign information of the user, and update the scene data based on the scene update information.

The scene update information is referred to as the corresponding changes of the virtual scene, which is generated based on the collected user's behavior data. For example, when the user is running straight forward, the buildings, trees etc. in the virtual scene needs to go backwards. With the user runs faster, the buildings, the trees and other objects also go backward faster, so as to meet the real situation. After the scene update information of the backward scene is generated based on the behavior data of the user who moves forward, the scene data is updated based on the scene update information, so that a virtual scene conforming to the real situation, may be provided to the user continuously by the scene output device based on the updated scene data, so as to continuously facilitate a steady run, an accelerated run, a turn and other actions performed by the user according to the changes in the virtual scene.

The step S504 may be implemented by the running device of the running exercise equipment accordingly. The running device includes a host module, a drive control module of the corresponding action. The drive control module of the corresponding action may include any one or a combination of the elevation control module, the driving control module, the slope control module, and the vibration control module. In order to ensure that the user may feel the real scene, the running device needs to control the action of the running exercise equipment according to the scene update information. For example, when the user's running path needs to be turned, uphill or downhill in the virtual scene, the running device needs to adjust the running belt correspondingly. For example, the slope of the runway is changed, the runway is raised, the speed of the runway is decreased, etc., to simulate the real body sense of the user in the current virtual scene.

For example, when the up and down movement of the running belt needs to be adjusted, the host module is configured to acquire the first action control information based on the scene update information, wherein the first action control information includes a up and down moving distance and up and down moving time of the running belt. The elevation control module, configured to adjust the up and down action of the running belt according to the first action control information, so as to make the user perceive a different gravitational acceleration. It is necessary to use the elevation control module to perform the up and down movement control of the running belt when the user performs actions such as an uphill movement, downhill movement, and a jump.

When the driving speed of the running belt needs to be adjusted, the host module is configured to acquire the second action control information based on the scene update information, wherein the second action control information includes a driving speed of the running belt. The driving control module is configured to adjust the driving action of the running belt according to the second action control information. It is necessary to use the driving control module to perform the driving speed control of the running belt when the user performs an action such as an accelerated or decelerated run.

When the slope of the running belt needs to be adjusted, the host module is configured to acquire the third action control information based on the scene update information, wherein the third action control information includes a tilt angle and tilt time of the running belt. The slope control module is configured for adjusting a tilt action of the running belt according to the third action control information. By controlling different tilt angles of the running belt, various scenes, such as the front and back slope, the left and right slope, or combinations thereof may be simulated. It is necessary to use the slope control module to control the slope of the running belt when the user is located on a sloping road or running uphill or downhill.

When the vibration of the running belt needs to be controlled, the host module is configured to acquire the fourth action control information based on the scene update information, wherein the fourth action control information includes vibration intensity and vibration time of the running belt. The vibration control module is configured for adjusting the vibration action of the running belt according to the fourth action control information, to simulate the vibration of the ground in the virtual scene or send an alarm or prompt to the user through the vibration.

As suggested above, the present invention provides a solution which combines a running exercise equipment and virtual reality technology, to provide a virtual scene to the user based on the preset scene data, so that the scene that the user sees is no longer confined to the place where the running exercise equipment is placed, and the user will perform the corresponding actions based on the virtual scene. The scene update information is generated by acquiring the behavior data of the user when performing actions, thereby updating the scene data, so that the virtual scene provided to the user may be advanced and changed according to the action of the user. At the same time, the actions of the running exercise equipment are controlled based on the scene update information, so that the user is capable of physically obtaining the physical experience caused by changes of the scene, thereby improving the user experience when exercising on the running exercise equipment.

It should be noted that the present invention may be implemented in software and/or a combination of software and hardware. For example, an application specific integrated circuit (ASIC), a general purpose computer, or any other similar hardware device may be used to realize the present invention. In one embodiment, the software program of the present invention may be executed by a processor to achieve the steps or functions described above. Likewise, the software program (including the associated data structure) of the present invention may be stored in a computer-readable recording medium, such as a RAM memory, a magnetic drive, an optical drive or a floppy disk and similar devices. Besides, some of the steps or functions of the present invention may be implemented using hardware, for example, a circuit which cooperates with a processor and performs each step or function.

Additionally, a part of the present invention may be applied as a computer program product, such as a computer program instruction. When the computer program instruction is being executed by a computer, a method and/or technical solution of the present invention may be invoked or provided through the computer operation. And the program instructions that is used to invoke the method of the present invention may be stored in a fixed or movable recording medium, and/or transmitted through broadcast or a data stream in other signal carrying medium, and/or stored in a working memory of the computer device which runs based on the program instructions. Thus, in accordance with one embodiment of the present invention, a device is provided, wherein the device includes a memory for storing computer program instructions and a processor for executing the program instructions. Wherein, when the computer program instructions are being executed by the processor, the device is triggered to perform the above methods and/or technical solutions according to various embodiments of the present invention.

As to the ordinary skilled person in the art, the present invention is not limited to the details of the illustrative embodiment as above. And the present invention may be realized in other specific forms without departing from the spirit or essential characteristics of the present invention. Thus, no matter from which point of view, the invention is to be considered as illustrative and not restrictive, and the scope of the present invention is defined by the appended claims rather than the above description. Therefore, the changes within the connotations and scope of equivalents of the claims all fall in the present invention. Any reference signs in the claims should not be regarded as a limitation to the claims. In addition, the term "including" does not exclude other units or steps, and the singular does not exclude the plural. The plurality of units or devices described in the device claims may also be implemented by one unit or device via software or hardware. The "first", "second" and other words are just used to express the name and do not indicate any particular order.

What is claimed is:

1. A virtual reality interaction method in a running exercise equipment, comprising:
    providing a virtual scene to a user according to scene data;
    acquiring behavior data of a user when the user performs an action according to the virtual scene;
    generating scene update information according to the behavior data of the user, and updating the scene data according to the scene update information; and
    controlling an action of the running exercise equipment according to the scene update information;
    wherein, the behavior data is acquired by providing a plurality of 3D cameras distributed around the user, to capture motion postures of the user in real time and converting the motion postures into a human spatial motion vector matrix in real time;
    coordinates of the human spatial motion vector matrix include a human key feature point matrix, motion trend and velocities related to the human key feature point matrix, and displacement coordinates related to the human key feature point matrix.

2. The method according to claim 1, wherein the behavior data includes action characteristic information and sign information.

3. The method according to claim 2, wherein the method further includes providing the sign information to the user.

4. The method according to claim 1, wherein the step of controlling the action of the running exercise equipment according to the scene update information includes:
    acquiring first action control information according to the scene update information, wherein the first action control information includes an up and down moving distance of a running belt and/or up and down moving time of the running belt; and adjusting an up and down moving action of the running belt according to the first action control information.

5. The method according to claim 1, wherein the step of controlling action of the running exercise equipment according to the scene update information includes:

acquiring second action control information according to the scene update information, wherein the second action control information includes a driving speed of a running belt; and adjusting a driving action of the running belt according to the second action control information.

6. The method according to claim 1, wherein the step of controlling the action of the running exercise equipment according to the scene update information includes:

acquiring third action control information according to the scene update information, wherein the third action control information includes a tilt angle and tilt time of a running belt; and adjusting a tilt action of the running belt according to the third action control information.

7. The method according to claim 1, wherein the step of controlling the action of the running exercise equipment according to the scene update information includes:

acquiring fourth action control information according to the scene update information, wherein the fourth action control information includes vibration intensity and vibration time of a running belt; and adjusting a vibration action of the running belt according to the fourth action control information.

8. The method according to claim 1, wherein:

the step of providing a virtual scene to the user according to the scene data is realized by a scene output device;

the step of acquiring behavior data of a user when the user performs an action according to the virtual scene is realized by a user data acquisition device;

the step of generating scene update information according to the behavior data of the user and updating the scene data according to the scene update information is realized by a scene update module; and the step of controlling the action of the running exercise equipment according to the scene update information is realized by a running device.

9. The method according to claim 8, wherein the scene output device includes at least one device selecting from the group consisting of a VR device and a projection device.

10. The method according to claim 8, wherein the user data acquisition device includes at least one device selecting from the group consisting of a 3D camera, a three-axis gyroscope, and a sensor.

11. The method according to claim 8, wherein the scene update module includes a processor integrated in the scene output device or the running device.

12. The method according to claim 8, wherein the running device includes a running platform, a running belt arranged on the running platform, and a motor for driving the running belt.

13. A non-transitory computer-readable storage medium, storing one or more computer-readable instructions operative, when executed by one or more processors, to cause the one or more processors to:

providing a virtual scene to a user according to the scene data;

acquiring behavior data of a user when the user performs an action according to the virtual scene;

generating scene update information according to the behavior data of the user, and updating the scene data according to the scene update information; and controlling the action of the running exercise equipment according to the scene update information;

wherein, the behavior data is acquired by providing a plurality of 3D cameras distributed around the user, to capture motion postures of the user in real time and converting the motion postures into a human spatial motion vector matrix in real time;

coordinates of the human spatial motion vector matrix include a human key feature point matrix, motion trend and velocities related to the human key feature point matrix, and displacement coordinates related to the human key feature point matrix.

14. A running exercise equipment, comprising:

one or more processors;

one or more non-volatile storage media, storing one car more computer-readable instructions operative, when executed by the one or more processors, to cause the one or more processors to:

provide a virtual scene to a user according to the scene data;

acquiring behavior data of a user when the user performs an action according to the virtual scene;

generate scene update information according to the behavior data of the user, and updating the scene data according to the scene update information; and control an action of the running exercise equipment according to the scene update information;

wherein, the behavior data is acquired by providing a plurality of 3D cameras distributed around the user, to capture motion postures of the user in real time and converting the motion postures into a human spatial motion vector matrix in real time;

coordinates of the human spatial motion vector matrix include a human key feature point matrix, motion trend and velocities related to the human key feature point matrix, and displacement coordinates related to the human key feature point matrix.

15. The running exercise equipment according to claim 14, wherein the running exercise equipment includes a scene output device, the scene output device includes at least one of the one or more processors and at least one of the one or more non-volatile storage media, when the one or more computer-readable instructions stored in the non-volatile storage medium of the scene output device are executed by the one or more processors in the scene output device, cause the one or more processor of the scene output device to: providing a virtual scene to the user according to the scene data.

16. The running exercise equipment according to claim 14, wherein the running exercise equipment includes a user data acquisition device, the user data acquisition device includes at least one of the one or more processors and at least one of the one or more non-volatile storage media, when the one or more computer-readable instructions stored in the non-volatile storage medium of the user data acquisition device are executed by the one or more processors in the user data acquisition device, cause the one or more processors of the user data acquisition device to: acquiring behavior data of a user when the user performs an action according to the virtual scene.

17. The running exercise equipment according to claim 14, wherein the running exercise equipment includes a scene update module, the scene update module includes at least one of the one or more processors and at least one of the one or more non-volatile storage media, when the one or more computer-readable instructions stored in the non-volatile storage medium of the scene update module are executed by the one or more processors in the scene update module, cause the one or more processors of the scene update module to: generating scene update information according to the behavior data of the user, updating the scene data according to the scene update information.

18. The running exercise equipment according to claim 14, wherein the running exercise equipment includes a running device, the running device includes at least one of the one or more processors and at least one of the one or more non-volatile storage media, when the one or more computer-readable instructions stored in the non-volatile storage medium of the running device are executed by the one or more processors in the running device, cause the one or more processors of the running device to: controlling an action of the running exercise equipment according to the scene update information.

* * * * *